United States Patent [19]

Tsuchida et al.

[11] Patent Number: 5,194,603
[45] Date of Patent: Mar. 16, 1993

[54] 5,10,15,20-TETRA(2',6'-DIPIVALOYLOXY-PHENYL)PORPHINATO METAL COMPLEX

[75] Inventors: Eishun Tsuchida, Tokyo; Teruyuki Komatsu, Tachikawa; Etsuo Hasegawa, Omiya; Hiroyuki Nishide, Tokyo, all of Japan

[73] Assignee: Nippon Oil & Fats Co., Ltd., Tokyo, Japan

[21] Appl. No.: 601,715

[22] PCT Filed: Mar. 13, 1990

[86] PCT No.: PCT/JP90/00321

§ 371 Date: Oct. 29, 1990

§ 102(e) Date: Oct. 29, 1990

[87] PCT Pub. No.: WO90/15803

PCT Pub. Date: Dec. 27, 1990

[30] Foreign Application Priority Data

Jun. 19, 1989 [JP] Japan .................................. 1-156331

[51] Int. Cl.$^5$ .......................................... C07D 487/22
[52] U.S. Cl. ..................................................... 540/145
[58] Field of Search ......................................... 540/145

[56] References Cited

PUBLICATIONS

Chemistry Letters: "A bisfenced porphynatoring system . . . synthesis and ligand binding" pp. 1071–1074 (1990).

"Phosphocholine-substituted 5,10,15,20-Tetrapenyl-porphyrinatoiron Oxygen Carrier under physiological Conditions", *J. Chem. Soc. Dalton Trans*, 1985, Eishun Tsuchida et al., Tokyo, Japan.

"Lipsomal Heme as Oxygen carrier under Semi-physiological Conditions", Eishun Tsuchia et al., *J. Chem. Soc. Dalton Trans*, 1984, Tokyo, Japan.

*Primary Examiner*—Robert T. Bond
*Assistant Examiner*—Jyothsna Venkat
*Attorney, Agent, or Firm*—Antonelli, Terry, Stout & Kraus

[57] ABSTRACT

The present invention relates to a porphyrin metal complex represented by the formula (1):

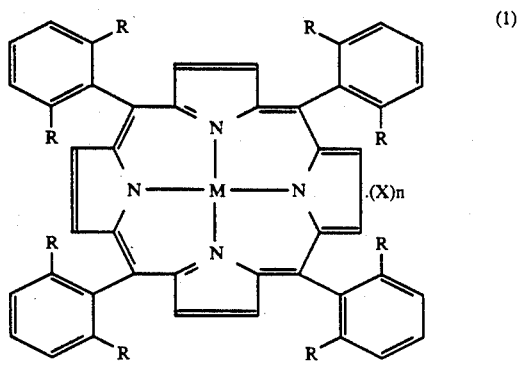

wherein R is a pivaloyloxy group, M is a transition metal ion of the group IV and the group V metals, X is a halogen ion, and n is 0 or 1.

The above compound is used as a more stable artificial oxygen carrier capable of preventing the behavior of oxidation and deterioration.

3 Claims, No Drawings

5,10,15,20-TETRA(2',6'-DIPIVALOYLOXY-PHENYL)PORPHINATO METAL COMPLEX

TECHNICAL FIELD

The present invention relates to porphyrin metal complexes which are used as artificial oxygen carriers and the like.

BACKGROUND ART

An iron (II) porphyrin complex contained in hemoglobin or myoglobin reversibly adsorbs and desorbs oxygen molecules. Many studies for producing synthetic complexes which have oxygen adsorption and desorption functions similar to those of natural porphyrin iron (II) complexes have been reported: J. P. Collman, Accounts of Chemical Research, 10, 265(1977), and F. Basolo, B. M. Hoffman and J. A. Ibers, ibid, 8, 384(1975). As a porphyrin iron (II) complex from which a stable oxygen complex is produced at room temperature, an iron (II) 5,10,15,20-tetra($\alpha$, $\alpha$, $\alpha$, $\alpha$-o-pivalamidephenyl)porphyrin complex is reported (J. P. Collman et al., The Journal of the American Chemical Society, vol. 97, p.1427(1975)).

However, the complex is unable to produce a stable oxygen complex because it is easily oxidized by oxygen in the presence of a small amount of water. Accordingly, an iron (II) porphyrin complex which produces a stable oxygen complex at room temperature has been continuously researched. The inventors of the present invention have found that oxygen is reversibly adsorbed and desorbed in an aqueous solution by inclusion of these iron porphyrin complexes in lipid molecular membranes. (Publication number of examined patent application: 59-25767/1984 and Publication number of laid-open patent application: 59-101490/1984).

DISCLOSURE OF INVENTION

As a result of an investigation into molecular designs for porphyrin metal complexes producible more stable oxygen complexes and the appearance of their functions, the present inventors considered that the behavior of oxidation and deterioration of the complexes was prevented by introducing bulky substituent groups in both sides of the porphyrin rings so that more stable oxygen complexes could be provided and they have found new porphyrin metal complexes.

Namely, the present invention provides a porphyrin metal complex (5,10,15,20-tetra(2',6'-dipivaloyloxyphenyl)porphinato metal complex) which is represented by the formula (1):

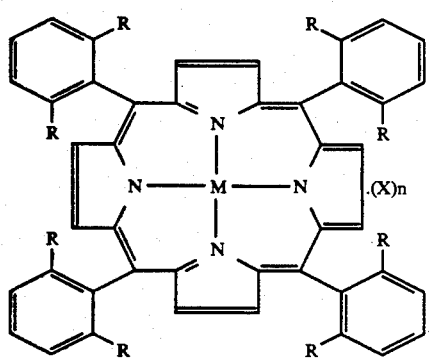

wherein R is a pivaloyloxy group, M is a transition metal ion of the group IV and the group V metals, X is a halogen ion, and n is 0 or 1. The same marks undermentioned show the same meanings.

As the transition metal ion, an iron ion or a cobalt ion is especially preferred. As the halogen ion, a chlorine ion or a bromin ion can be exemplified. The coordination number of the ion is given by the valence of metal ion M minus 2. The valence of the metal ion is generally 2 or 3.

A complex connectable with oxygen is embodied by a complex having a divalent metal ion of two valence and one or two basic axial ligands. The complex is represented by the formula (2):

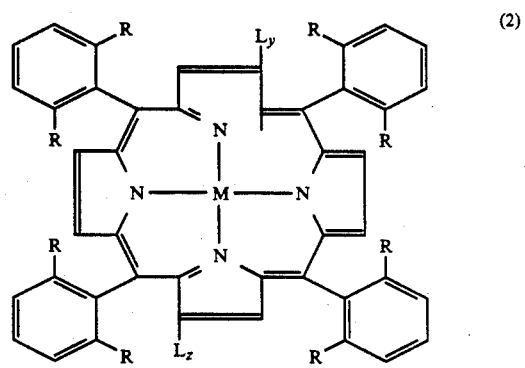

wherein L is a basic axial ligand, y and z are 0 or 1, respectively, and y+z is 1 or 2.

The porphyrin metal complexes represented by the formula (1) can be synthesized by the following process, for example;

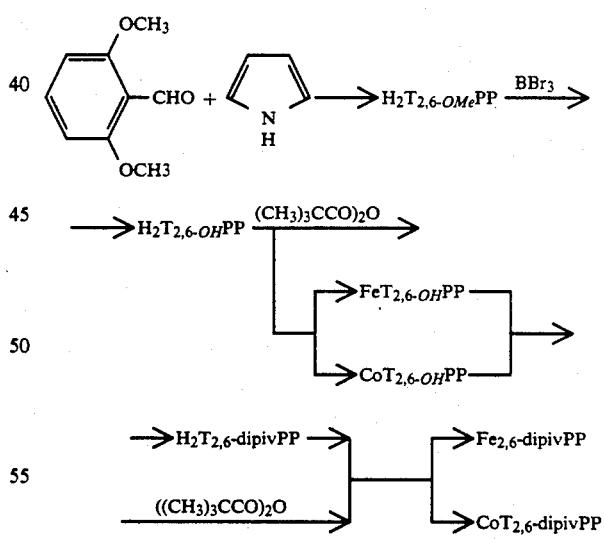

In the above-mentioned process, 2,6-dimethoxybenzaldehyde and pyrrole (equimolecular quantities) are condensed in a suitable solvent to synthesize 5,10,15,20-tetra(2',6'-dimethoxyphenyl)porphyrin (in the above process, the compound represented by $H_2T_{2,6\text{-}OMe}PP$).

As the solvent, acetic acid, propionic acid, butyric acid or the like is usable. The reaction temperature can be controlled by considering the kind of the solvent and the other conditions, usually a temperature of 80°-120° C. is selected. The reaction time is 5-12 hours, preferably 5-8 hours. After such condensation of these compounds, the tarry reaction mixture obtained by filtrating the reaction solution is purified by, for example, silica gel chromatography or the like to obtain 5,10,15,20-tetra(2',6'-dimethoxyphenyl)porphyrin. Then, 5,10,15,20-tetra(2',6'-dimethoxyphenyl)porphyrin is dissolved in a suitable dry solvent (dichloromethane, chloroform, tetrahydrofuran or the like), cooled in an ice-water bath 40 times or more of the molar quantity of boron tribromide is added and the mixture is stirred at room temperature for 10-24 hours. The reaction solution is poured dropwise into ice water, the solution is extracted by an organic solvent such as ethyl acetate, the organic layer is evaporated to dryness, and the solid is purified by silica gel chromatography to obtain 5,10,15,20-tetra(2',6'-dihydroxyphenyl)porphyrin (in the above process, the compound represented by $H_2T_{2,6-OH}PP$).

Then, a solution of 5,10,15,20-tetra(2',6'-dihydroxyphenyl)porphyrin in dry tetrahydrofuran is refluxed at the boiling point in an atmosphere of nitrogen, pivalic anhydride (40 times of the molar quantity) is added and then a small quantity of 4-dimethylaminopyridine is added. The mixture is refluxed for 10-24 hours. The reaction mixture is extracted by a suitable organic solvent (such as dichloromethane, chloroform, ether or the like), and the resulting solution is washed with dilute hydrochloric acid and with water. The organic layer is collected and the solvent is distilled away. The residue obtained is purified by, for example, silica gel chromatography to obtain a porphyrin coordinating no metal M (in the above process, the compound represented by $H_2T_{2,6}$-dipivPP).

The central metal is introduced to the porphyrin thus obtained by a common method (for example, edited by David Drophin, The porphyrins, volume I, pages 390-483, 1978, Academic Press Company) and 5,10,15,20-tetra(2',6'-dihydroxyphenyl)porphinato iron (in the above process, the compound represented by $FeT_{2,6-OH}PP$) or a cobalt derivative (in the above process, the compound represented by $CoT_{2,6-OH}PP$) is obtained. In general, as the iron complex, a porphinato iron (III) complex is obtained. As the cobalt complex, a porphinato cobalt (II) complex is obtained.

On the other hand, a solution of 5,10,15,20-tetra(2',6'-dihydroxyphenyl)porphyrin in dry tetrahydrofuran is refluxed at the boiling point in an atmosphere of nitrogen, pivalic anhydride (40 times of the molar quantity) is added and then a small quantity of 4-dimethylaminopyridine is added. The mixture is refluxed for 10-24 hours. The reaction mixture is extracted by a suitable organic solvent (such as dichloromethane, chloroform, ether or the like), and the resulting solution is washed with dilute hydrochloric acid and with water. The organic layer is collected and the solvent is distilled away under reduced pressure. The residue obtained is purified by, for example, silica gel chromatography to obtain a porphyrin having no metal M (in the above process, the compound represented by $H_2T_{2,6}$-dipivPP).

Further, the above-mentioned metal porphyrin complexes coordinating a metal ion (in the above process, the compounds represented by $FeT_{2,6-OH}PP$ and $CoT_{2,6-OH}PP$) are reacted with pivalic anhydride by the same method as aforesaid to obtain 5,10,15,20-tetra(2',6'-dipivaloyloxyphenyl)porphinato iron (in the above process, the compound represented by $FeT_{2,6}$-dipivPP) and 5,10,15,20-tetra(2',6'-dipivaloyloxyphenyl)porphinato cobalt (in the above process, the compound represented by $CoT_{2,6}$-dipivPP) are obtained, respectively.

The porphyrin metal complex represented by the formula (2) is obtained from the porphinato iron (III) complex or the porphinato cobalt (II) complex obtained by the above method as follows.

Namely, in the case of the porphinato iron (III) complex, it is obtained by reduction of the center iron (III) to (II) by using a suitable reducing agent (for example, sodium dithionite, ascorbic acid, etc) in the usual way in the presence of suitable axial ligands (L). In the case of the porphinato cobalt (II) complex, the porphinato metal complex represented by the formula (2) is obtained only by addition of suitable axial ligands (L).

Moreover, the introduction of a metal ion M to the porphirin ring may be conducted after adding pivalic anhydride, that is, a metal ion can be inserted into 5,10,15,20-tetra(2',6'-dipivaloyloxyphenyl)porphyrin.

The porphyrin metal complexes represented by the formula (2) thus obtained are embedded in a liposomal bilayer membrane comprised of lipid in neutral water, so that more stable dioxygen complexes are produced in contact with oxygen. Then, these complexes adsorb and desorb oxygen depending on the partial pressure of oxygen. The adsorption and desorption of oxygen are achievable reversibly and repeatedly. The complex acts as an oxygen adsorption and desorption agent or an oxygen carrier.

BEST MODE FOR CARRYING OUT THE INVENTION

Embodiments for synthesizing compounds represented by $H_2T_{2,6}$-dipivPP in the above process:

(A) 1500 ml of a solution of 20 g of 2,6-dimethoxybenzaldehyde in propionic acid was heated at 100° C. with stirring, 8.05 g of pyrrole was added and the mixture was continuously heated with stirring for 7 hours. After cooling to room temperature, the mixture solution was left overnight. The reaction solution was filtered through a glass filter, and the filtrate was washed with cooled methanol and purified with a silica gel column (dichloromethane) to obtain 5,10,15,20-tetra(2',6'-dimethoxyphenyl)porphyrin.

Yield: 3.8 g (15%). Thin-layer chromatography (Merck silica gel plate, dichloromethane): Rf=0.60 (mono spot). Infrared absorption spectra (NaCl, cm$^{-1}$): 1580($\nu_{c=c}$(phenyl nucleus)), 1280($\nu_{c-o-c}$(methoxy)). Visible absorption spectra (CH$_2$Cl$_2$), $\lambda_{max}$ 642, 588, 544, 512, 420 nm. $^1$H-nuclear magnetic resonance spectra (CDCl$_3$, TMS standard, $\delta$(ppm)) 8.8(8H, s, pyrrole), 3.5(24H, s, —OCH$_3$), −2.8(2H, s, inner NH).

(B) 50 ml of a solution of 3.0 g of 5,10,15,20-tetra(2',6'-dimethoxyphenyl)porphyrin in dichloromethane was ice-cooled with stirring, 35.2 g of boron tribromide was added, and the mixture was stirred for about two hours with ice-cooling and then for about 20 hours at room temperature. The reaction mixture was added dropwise in ice water and the solution was extracted with 250 ml of ethyl acetate. The extract was washed with an aqueous solution of 5% sodium bicarbonate and with water. The chloroform layer was dehydrated by using anhydrous sodium sulfate and filtered, and the filtrate was evaporated to dryness. The residue obtained was fractionated and purified by chromatography on a column of silica gel (ethyl acetate / methanol (20/1) (volume/volume)). The object fractionated was collected and evaporated to dryness.

Yield: about 2.4 g (about 92%). Infrared absorption spectra (NaCl, cm$^{-1}$): 3350($\nu_{OH}$), 1580($\nu_{c=c}$(phenyl nucleus)), Visible absorption spectra (CH$_3$OH, $\lambda_{max}$ 643, 585, 546, 512, 415 nm). $^1$H-nuclear magnetic resonance spectra (CD$_3$OD, TMS standard, $\delta$(ppm)) 8.8(8H, s, pyrrole), −2.8(2H, s, inner NH).

(C) 50 ml of a solution of 1.0 g of 5,10,15,20-tetra(2',6'-dihydroxyphenyl)porphyrin in dry tetrahydrofuran was refluxed at the boiling point in an atmosphere of nitrogen. 5.0 g of anhydrous pivalic acid and then 0.17 g of 4-dimethylaminopyridine were added to the solution, and the mixture was heated under reflux for about 20 hours. The reaction solution was evaporated and the residue obtained was dissolved in 250 ml of chloroform. The chloroform solution was washed with dilute hydrochloric acid and with water. The solution was dehydrated by using anhydrous sodium sulfate and filtered, and the filtrate was evaporated to dryness. The residue obtained was fractionated and purified by chromatography on a column of silica gel (chloroform / ether (10/1) (volume/volume)). The object fractionated was collected and evaporated to dryness under reduced pressure. Thus, 5,10,15,20-tetra(2',6'-dipivaloyloxyphenyl)porphyrin was obtained as violet needle crystals. Yield: 1.15g (60%).

Elemental analysis (weight %): C 67.66(67.8), H 7.14(6.9), N 3.48(3.8)(Calculated values for C$_{84}$H$_{94}$N$_4$O$_{16}$·4H$_2$O were designated in parentheses). Infrared absorption spectra (NaCl, cm$^{-1}$): 1760 ($\nu_{c=o}$(ester)), 1580($\nu_{c=c}$(phenyl nucleus)), Visible absorption spectra (CHCl$_3$), $\lambda_{max}$ 637, 583, 536, 507, 412 nm. $^1$H-nuclear magnetic resonance spectra (CDCl$_3$, TMS standard, $\delta$(ppm)) 8.8(8H, s, pyrrole), 7.4-7.9(12H, m, phenyl-H), −0.3(72H, s, pivaloyl), −2.8(2H, s, inner NH). $^{13}$C-nuclear magnetic resonance spectra (CDCl$_3$, TMS standard).

| Number | $\delta$(ppm) |
| --- | --- |
| ($\alpha$) | 146.87 |
| ($\beta$) | 131.22 |
| (m) | 108.99 |
| (1) | 129.63 |
| (2) | 151.82 |
| (3) | 120.17 |
| (4) | 128.19 |
| (5) | 175.53 |
| (6) | 38.00 |
| (7) | 25.71 |

Numerical values in parentheses designated the following carbon.

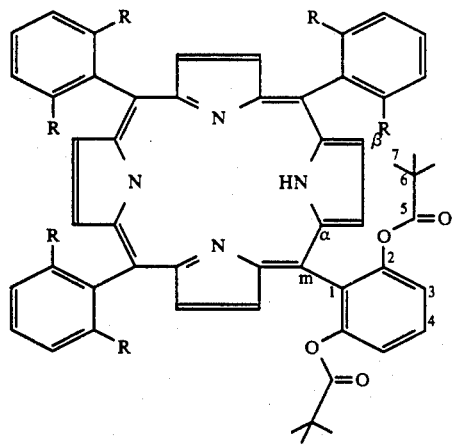

EXAMPLE 1

1.0 g of 5,10,15,20-tetra(2',6'-dihydroxyphenyl) porphyrin synthesized in the above embodiment (B) was dissolved in 50 ml of dry dimethylformamide, and the atmosphere was replaced with nitrogen. To the solution, 5.37 g of ferrous chloride (FeCl$_2$4H$_2$O) was added, and then the mixture was refluxed by heating. After 6 hours, the solvent was evaporated to dryness under reduced pressure, and the residue obtained was dissolved in 250 ml of ethyl acetate. The ethyl acetate solution was washed with dilute hydrochloric acid and with water. The ethyl acetate layer was dehydrated by using anhydrous sodium sulfate and filtered, and the filtrate was evaporated to dryness. The residue obtained was fractionated and purified by chromatography on a column of silica gel (ethyl acetate / methanol (20/1) (volume/volume). The object fractionated was collected and evacuated to dryness under reduced pressure.

Yield: 1.12 g (78%). Visible absorption spectra (CH$_3$OH), $\lambda_{max}$ 680, 650, 579, 509, 416 nm.

In the above embodiment (C), using the same method except that 5,10,15,20-tetra(2',6'-dihydroxyphenyl)porphinato iron was used instead of 5,10,15,20-tetra(2',6'-dihydroxyphenyl)porphyrin, 5,10,15,20-tetra(2',6'-dipivaloyloxyphenyl)porphinato iron was synthesized.

FAB mass spectrometry: [M]$^+$ = 1503.

Elemental analysis (weight %): C 66.21(66.2), H 6.58(6.2), N 3.31(3.7)(Calculated values for C$_{84}$H$_{92}$N$_4$O$_{16}$FeCl·H$_2$O were designated in parentheses). Infrared absorption spectra (NaCl, cm$^{-1}$): 1760 ($\nu_{c=o}$(ester)), 1580($\nu_{c=c}$(phenyl nucleus)), Visible absorption spectra (CHCl$_3$), $\lambda_{max}$ 680, 650, 579, 508, 416 nm.

EXAMPLE 2

1.0 g of 5,10,15,20-tetra(2',6'-dihydroxyphenyl) porphyrin synthesized in the above embodiment (B) was dissolved in 50 ml of dry tetrahydrofuran, and the atmosphere was replaced with nitrogen. To the solution, 3.5 g of cobalt (II) chloride (Co(II)Cl$_2$) and 0.43 g of 2,6-lutidine was added, and then the mixture was refluxed by heating. After 3 hours, the solvent was evaporated to dryness, and the residue obtained was dissolved in 250 ml of ethyl acetate. The ethyl acetate solution was washed with dilute hydrochloric acid and with water. The ethyl acetate layer was dehydrated by using anhydrous sodium sulfate and filtered, and the filtrate was evaporated to dryness. The residue obtained was fractionated and purified by chromatography on a column of silica gel (ethyl acetate / methanol (20/1) (volume/volume)). The object fractionated was collected and evacuated to dryness under reduced pressure.

Yield: 0.98 g (91%). Visible absorption spectra (CH$_3$OH), $\lambda_{max}$ 553, 521, 404 nm.

In Example 1 (C), using the same method except that 5,10,15,20-tetra(2',6'-dihydroxyphenyl)porphinato cobalt (II) was used instead of 5,10,15,20-tetra(2',6'-dihydroxyphenyl)porphyrin, 5,10,15,20-tetra(2',6'-dipivaloyloxyphenyl)porphinato cobalt II) was synthesized.

Elemental analysis (weight %): C 67.83(67.7), H 6.84(6.4), N 3.36(3.7)(Calculated values for C$_{84}$H$_{92}$N$_4$O$_{16}$Co·H$_2$O were designated in parentheses). Infrared absorption spectra (NaCl, cm$^{-1}$) 1760 ($\nu_{c=o}$(ester)), 1580($\nu_{c=c}$(phenyl nucleus)), Visible absorption spectra (CHCl$_3$), $\lambda_{max}$ 553, 522, 403 nm.

REFERENCE EXAMPLE 1

10 ml of anhydrous toluene solution containing 0.75 mg (0.5 μmol) of 5,10,15,20-tetra(2',6'-dipivaloyloxyphenyl)porphinato iron (III) synthesized in Example 1 was prepared and the atmosphere was replaced with nitrogen. The solution and an aqueous solution of sodium dithionite were mixed with stirring in heterogeneous system, and iron (III) was reduced to iron (II). Only toluene layer was collected in an atmosphere of nitrogen, and dehydrated with anhydrous sodium sulfate and then filtered. 82.11 mg (0.1 mmol) of 1-methylimidazole was added to the toluene solution obtained, and the solution was charged in a quartz cell for measuring visible absorption spectra and the cell was sealed. Thus, a toluene solution of iron (II)-5,10,15,20-tetra(2',6'-dipivaloyloxyphenyl)porphyrin-bis(1-methylimidazole) complex was obtained.

The visible absorption maxima $\lambda_{max}$ of the ferrous complex obtained were 561, 535 and 429 nm which corresponded to those of a deoxy type.

These peaks of the visible absorption spectra changed rapidly after blowing oxygen gas into the solution, and the new peaks of $\lambda_{max}$ 544 and 426 nm appeared. It shows that an oxygenated complex was obtained. When nitrogen gas was blown into the oxygenated complex solution for one minute or the solution was degassed by freezed-thaw method, visible absorption spectra were reversibly changed from the oxygenated type to the deoxy type. It was confirmed by the spectra that the complex reversibly adsorbed and desorbed oxygen. Furthermore, when oxygen and then nitrogen were repeatedly blown into the solution in a series of operations, oxygen was alternately adsorbed and desorbed.

REFERENCE EXAMPLE 2

A chloroform solution containing 0.75 mg (0.5 μmol) of 5,10,15,20-tetra(2',6'-dipivaloyloxyphenyl)porphinato iron synthesized in Example 1, 23.61 mg (0.1 mmol) of 1-laurylimidazole and 68.7 mg (0.1 mmol) of dimyristoylphosphatidylcholine was evaporated to dryness with a rotary evaporator to form a film. 20 ml of 1/15 M phosphoric acid buffer adjusted to pH 7.0–8.0 was added and the solution was irradiated with ultrasonic waves (60 W, 10 minutes). The gas in the solution was replaced by nitrogen, and a small amount of ascorbic acid solution was added to the solution, and the solution was charged in a measuring quartz cell and the cell was sealed. Thus, liposome solution containing iron (II)-5,10,15,20-tetra(2',6'-dipivaloyloxyphenyl)porphyrin-bis(1-laurylimidazole) complex was obtained.

The visible absorption maxima $\lambda_{max}$ of the complex obtained were 562, 536 and 432 nm which show a deoxy type.

These peaks of the spectra changed rapidly by blowing oxygen gas into the solution, and the peaks of $\lambda_{max}$ 547 and 424 nm appeared. It shows that an oxygenated complex was obtained. When nitrogen gas was blown into the oxygenated complex solution for one minute or the solution was degassed by the freezed-thaw method, the visible absorption spectra were reversibly changed from the oxygenated type to the deoxy type. It was confirmed by the spectral change that the complex reversibly adsorbed and desorbed oxygen. Furthermore, when oxygen and then nitrogen were repeatedly blown into the solution in a series of operations, oxygen was alternately adsorbed and desorbed.

INDUSTRIAL APPLICABILITY

As to a series of compounds having four bulky substituting groups which are compatible with phospholipid on one side of a porphyrin ring, the present inventors have already reported (E. Tsuchida, et al., Top. Curr. Chem., 132, 63 (1986); E. Tsuchida, et al., Macromolecules, 21, 3119 (1988)). The present invention provides new porphyrin metal complexes having four bulky substituting groups on each side, not only on one side but also on the other side, of a porphyrin ring. The compounds are expected to use as artificial oxygen carriers of an unknown type.

We claim:

1. A porphyrin metal complex represented by the formula (1):

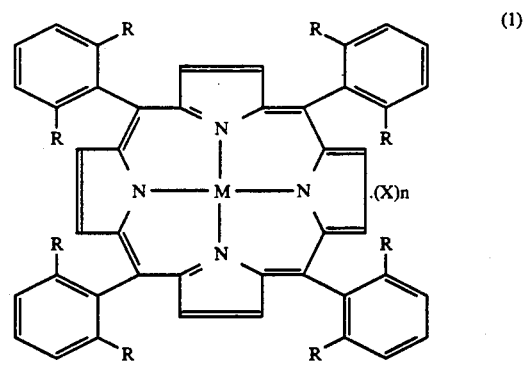

wherein R is a pivaloyloxy group, M is a transition metal ion of the group IV and the group V metals, X is a halogen ion, and n is 0 or 1.

2. A porphyrin metal complex according to claim 1, wherein M is Fe or Co ion.

3. A porphyrin metal complex according to claim 1, wherein M is divalent or trivalet Fe or Co ion.

* * * * *